US005601800A

United States Patent [19]
Katti et al.

[11] Patent Number: 5,601,800
[45] Date of Patent: Feb. 11, 1997

[54] NEW MULTIFUNCTIONAL LIGANDS FOR POTENTIAL USE IN THE DESIGN THERAPEUTIC OR DIAGNOSTIC RADIOPHARMACEUTICAL IMAGING AGENTS

[75] Inventors: Kattesh V. Katti; Wynn A. Volkert; Alan R. Ketring; Prahlad R. Singh, all of Columbia, Mo.

[73] Assignee: Curators of the University of Missouri, Columbia, Mo.

[21] Appl. No.: 211,905

[22] PCT Filed: Nov. 9, 1992

[86] PCT No.: PCT/US92/09742

§ 371 Date: Jul. 29, 1994

§ 102(e) Date: Jul. 29, 1994

[87] PCT Pub. No.: WO93/08839

PCT Pub. Date: May 13, 1993

Related U.S. Application Data

[63] Continuation-in-part of Ser. No. 790,579, Nov. 8, 1991, abandoned.

[51] Int. Cl.$^6$ .................................................. A61K 51/04
[52] U.S. Cl. ................... 424/1.77; 424/9.36; 424/9.361; 534/14; 556/26; 568/8
[58] Field of Search .................... 424/1.77, 9.32, 424/9.323, 9.36, 9.361; 534/14; 556/26; 568/8

[56] References Cited

U.S. PATENT DOCUMENTS

| | | | |
|---|---|---|---|
| 5,057,302 | 10/1991 | Johnson et al. | 424/1.1 |
| 5,071,965 | 12/1991 | Dunn et al. | 534/14 |
| 5,095,111 | 3/1992 | Lever et al. | 540/544 |
| 5,138,008 | 8/1992 | Montague et al. | 528/21 |

OTHER PUBLICATIONS

Spencer et al., *Radionuclides in Therapy*. CRC Press, Boca Raton, Florida 1987.

Andres et al., *Radionucleotides for Therapy*. Hoffman–LaRoche & Co., Ltd., Basel, Switzerland, 1986, pp. 9–20.

Harbert, J. C., *Radionuclide Therapy of Bone Pain*. Thime Medical Inc., New York, 1987.

Volkert et al., "Therapeutic radionuclides: production and decay property considerations" *J Nucl Med* 32;174–185, 1991.

Mausner et al., *Radiolabeled Monoclonal Antibodies for Imaging and Therapy*, ed. S. C. Srivastava, Plenum Publishing Corp., New York, 1988, pp. 149–163.

Andres et al. Radionuclides for therapy: A review in *Radionclides for Therapy*, eds. P. Schubiger and P. Hasler. Editones–Roche, Basel, Switzerland, 1986, pp. 9–20.

Wessels et al., "Radionuclide selection and model absorbed dose calculations for radiolabelled tumor associated antibodies" *Medi Phys* 11:638–645, 1984.

Srivastava et al., "Progress in research on ligands, nuclides and techniques for labeling monoclonal antibodies" *Nucl Med Biol* 18:589–603, 1991.

Fritzberg et al., "Specific and stable labeling of antibodies with $^{99m}$Tc with a diamide dithiolate chelating agent" *Proc. Nat'l Aca Sci*, 85:4025–4029, USA (1988).

Moi et al., "Copper chelates as probes in biological systems: stable copper complexes with macrocyclic bifunctional chelating agents" *Anal Biochem* 148;249–253, 1985.

Parker, D., "Tumour targeting with radiolabelled macrocycle antibody conjugates" *Chem Soc Rev* 19;271–291, 1990.

Baidoo, K., "Evaluation of a diaminedithiol–based bifunctional . . . " in *Technetium and Rhenium in Chemistry and Nuclear Medicine*, eds. Nicolini et al., Raven Press, NY, 3rd, Chapter 2, pp. 369–374, 1990.

Covell et al., "Pharmacokinetics of monoclonal immunoglobulin . . . " *Cancer Res* 46:3969–3978, 1986.

Rao et al., "Dependence of immunoreactivity and tumor uptake on on ratio of Tc . . . " *J Nucl Med* 29:815, 1988.

Krejcarek et al., "Covalent attachment of chelating groups to macromolecules" *Biochem Biophys Res Comm* 77:581–585, 1977.

Roselli et al., "Comparative biodistributions of Yttrium–and Indium–labelled monoclonal antibody B72.3 in athymic mice . . . " *J Nucl Med* 30:672–682, 1989.

Paik et al., "Interposition of different clinical linkages between antibody . . . " *Nucl Med Biol, Int J Radiat Appl Inst* [B] 16:475–481, 1989.

Fritzberg et al., "Rhenium–186–188 labeled antibodies . . ." in *Technetium and Rhenium in Chemistry and Nuclear Medicine*, eds. M. Nicolini et al., NY Raven Press, 3rd Ed. Chap. 2, pp. 615–622, 1990.

Dean et al., "New facile methods for stable labeling . . . " in *Technetium and Rhenium in Chemistry and Nuclear Medicine*, eds. M. Nicolini et al., NY Raven Press, 3rd Ed. Chap. 2, pp. 605–607, 1990.

Deutsch et al., "The inorganic chemistry of technetium . . . " in *Technetium and Rhenium in Chemistry and Nuclear Medicine*, eds. M. Nicolini et al., NY Raven Press, 3rd Ed. Chap. 2, pp. 13–22, 1990.

(List continued on next page.)

Primary Examiner—Gary E. Hollinden
Assistant Examiner—Michael G. Hartley
Attorney, Agent, or Firm—Kohn & Associates

[57] ABSTRACT

A class of diagnostic and therapeutic compounds derived from phosphinimines that include ligands containing either a single phosphinimine functionality or both a phosphinimine group and a phosphine or arsine group, or an aminato group, or a second phosphinimine moiety. These phosphinimine ligands are complexed to early transition metal radionuclides (e.g. $^{99m}$Tc or $^{186}$Re/$^{188}$Re) or late transition metals (e.g., $^{105}$Rh or $^{109}$Pd). The complexes with these metals $^{186}$Re/$^{188}$Re, $^{99m}$Tc and $^{109}$Pd exhibit a high in vitro and high in vivo stability. The complexes are formed in high yields and can be neutral or charged. These ligands can also be used to form stable compounds with paramagnetic transition metals (e.g. Fe and Mn) for potential use as MRI contrast agents. Applications for the use of ligands and making the ligands are also disclosed.

2 Claims, No Drawings

OTHER PUBLICATIONS

Wheldon et al., "The radiobiology of targeted radiotherapy-review" *Int J Radiat Biol* 58:1–21, 1990.

Breitz et al., "Phase I studies of [186]Re whole MAb . . . " *J Nucl Med* 31:725, 1990.

Deshpande et al., "Copper [67]Cu labeled monclonal antibody Lym–1 . . . " *J Nucl Med* 29;217–225, 1988.

Weininger et al., "[186]Re–HEDP as bone therapeutic radio-pharmaceuticals" *Nucl Med Biol* 14:223–232, 1987.

DiZio et al. "Progestin–Rhenium complexes: Potential metal–based imaging agents for steroid receptors" *J Nucl Med* 32:295, 1991.

Lamberts et al., "The clinical use of somatostation analgoues in the treatment of cancer" in *Bailler's Clinical Endocrinology and Metabolism*, Baillere Tindall Publishers, vol. 4; 1990, pp. 29–49.

Volkert et al., "Radiolabelled phosphonic acid chelates: Potential therapeutic agents for treatment of skeletal metastases" *Drugs of the Future* 14:799–811, 1989.

Dewanjee, M. K. "The chemistry of Tc–99m–labeled radiopharmaceuticals." *Semin Nucl Med* 20:5–27, 1990.

Nicolini et al., *Technetium and Rhenium in Chemistry and Nuclear Medicine*, 3rd edition, Raven Press, New York, 1990.

Kung et al., "Current and future radiopharmaceuticals for brain imaging with single photon emission computed tomography" *Semin Nucl Med* 20:290–302, 1990.

Volkert, W. A., "Stereoreactivity of $^{99m}$Tc chelates at chemical and physiological levels" in *Technetium and Rhenium in Chemistry and Nuclear Medicine*, Raven Press, NY 3rd ed., Chap 2, pp. 343–352, 1990.

Deutsch et al., "The chemistry of rhenium and technetium as related to the use of isotopes of these elements in therapeutic . . . " *Nucl Med Biol* 13:465–477, 1986.

Kelly et al., "Technetium–99m complexes of functionalized . . . " in *Technetium and Rhenium in Chemistry and Nuclear Medicine*, Raven Press, NY, 3rd ed., Chap. 2, pp. 405–412, 1990.

Krishnamurty et al., "Pharmacokinetics and clinical application . . . " *Semin Nucl Med* 20:130–149, 1990.

Taylor, A., "Radionuclide evaluation of renal function" *Crit Rev Diag Imaging* 32;1–36, 1991.

Suess et al., "[99m]Tc–d, 1–HMPAO uptake and glutathione content in brain tumors" *J Nucl Med* 32:1675–1681, 1991.

Runge, V., "Gd–DTPA: An IV contrast agent for clinical MRI" *Nucl Med Biol* 15:37, 1988.

Koenig et al., "Relaxmetry of magnetic resonance imaging contrast agents" in *Magnetic Resonance Annual*, ed. H. Kresoil, Raven Press, New York, 1987.

Saini et al., "Advances in contrast–enhanced MR imaging" *Am J Radiol* 156:235, 1991.

Abel et al., "The Chemistry of Phosphinimines" *Phosphorous Sulfur*, 9:235–266 (1981).

Katti et al., "Transition Metal Chemistry . . . " *Comments Inorg Chem*, 10:53–73 (1990).

Cramer et al., "Preparation, Structure . . . " *Organometallics* 7:841, (1990).

Katti et al., *Inorg Chem*. 28:3033, 1989.

Mazzi & Nicolini et at., In *Technetium and Rhenium in Chemistry and Nuclear Medicine*, Raven Press, New York, 1990.

Gansow et al., "Chelates and antibodies. Current methods and new directions." in *Cancer Imaging with Radiolabeled Antibodies*, ed. D. M. Goldenberg, Kluever Acad Publ, 1990, pp. 153–171.

Wu, R.S., "Novel bifunctional linkers for antibody chelation . . . " in *Cancer Imaging with Radiolabelled Antibodies*, ed. D. M. Goldenberg Kluever Acad Publ, 1990, pp. 215–232.

Subramanian et al., "Bifunctional chelating agents for radiometal . . . " in *Cancer Imaging with Radiolabeled Antibodies*, ed. D. M. Goldenberg Kluever Acad Publ, 1990, pp. 183–199.

Nunn, A. D., "Radiopharmaceuticals for imaging myocardial perfusion" *Semin Nucl Med* 20:111–118, 1990.

Eisenhut et al. "Iodine [131]labeled diphosphonates for paliative treat. of bone metastases: II. Preliminary clinical results with [131]I–BDP3". *J Nucl Med* 27:167–174, 1986.

Abrams et al., "[99m]Tc–human polycolonal IgG radiolabeled via the hydrazino nicotinamide derivative for imaging focal sites of injection in rats." *J Nucl Med* 31:2022–2028, 1990.

Krohn et al. "The advantages of protecting the antigen binding site during antibody labeling" *J Nucl Med* 32:122–123, 1991.

Eisenhut et al., "Synthesis and In Vivo testing of a bromobutyl substituted 1,2–Dithia–5,9–diazacycloundencane . . . " *Nucl Med Biol* 16:805, 1989.

Ballinger et al., "Tc–99m spiperone dithiocarbamate; a potential radiopharmaceutical for dopamine receptor imaging with SPECT" *Appl. Radiat. Isot.* 40:547, 1989.

DiZio et al. "Progestin–Rhenium complexes: metal–labeled steroids with high receptor binding affinity, potential receptor . . . " *Bioconj. Chem.* 2:353, 1991.

Thomas et al., "High oxydation state technetium and rhenium . . . " *Inorganic Chemca Acta* 190:231–235, 1991.

Abel, E. et al., "Some Triphenylphosphinimie Complexes of Zinc, Cadmium, Mercury, Rhodium and Palladium" *Inorganica Chimica Acts*, 37 (1979) 107–111.

Imhoff, P. "Stabilization of Rhodium(I)–and Iridium(I)–Alkyl Bonds by Intramolecular Coordination of an Iminophosphorane . . . " *Organometallics* 1991, 10, pp. 1421–1431.

Cotton, F. et al., "Preparation and Structural Characterization of Salts of Oxotetrachlorotechnetium (V)" *Inorganic Chemistry*, vol. 18, No. 11, pp. 3024–3029 (1979).

Katti, K. et al., "Synthesis of New Metallacycles of Rhenium(VII) Oxides: Migration of a Me Si Group to Form the cis–Dioxo . . . " *Inorganic Chemistry*, vol. 28, pp. 3033–3036 (1989).

5,601,800

NEW MULTIFUNCTIONAL LIGANDS FOR POTENTIAL USE IN THE DESIGN THERAPEUTIC OR DIAGNOSTIC RADIOPHARMACEUTICAL IMAGING AGENTS

GRANT REFERENCE

Research in this application was supported in part by a grant from the Department of Energy (DE-FG02-89ER60875) to one of the inventors (Wynn A. Volkert). The Government has certain rights in the invention.

This application is a 371 of PCT/US92/09742 filed on Nov. 9, 1992, and published as WO93/08839 on May 13, 1993. This application is a continuation-in-part of U.S. Ser. No. 07/790,579 filed Nov. 8, 1991, now abandoned.

TECHNICAL FIELD

The metal compounds formed are easily prepared, generally producing a single species, in high yields which are highly stable. $^{99m}$Tc compounds have potential for diagnostic imaging applications. The beta-emitting transition metal radionuclides (e.g. $^{186}$Re/$^{188}$Re, $^{109}$Pd, etc.) hold potential for therapeutic applications. Chelates of these ligands with paramagnetic metal ions hold potential as MRI contrast agents.

BACKGROUND OF THE INVENTION

Radiotherapeutic Agents

Radiotherapy using "non-sealed sources" by way of radiolabeled pharmaceuticals has been employed for several decades [1–3]. Less than a handful of therapeutic pharmaceuticals are currently in routine use in the United States and approved by FDA. Recently, there has been renewed interest in developing new agents due to the emergence of more sophisticated molecular carriers, such as monoclonal antibodies, more capable of selective targeting of cancerous lesions. In addition, the identification of different radionuclides [4–7] with different chemical properties that have physical decay properties that are desirable for therapeutic application has further spurred development of new agents.

Although there has been some success in treatment of specific malignant diseases, many problems remain to be solved in this area. For example, in most cancers, it has been difficult to provide acceptable selectivity in radiation doses delivered to target tissues relative to normal tissues. Successful development of new therapeutic radiopharmaceuticals will require improved localization of these agents in target tissues and increasing rates of clearance from non-target tissues. In both of these situations, it is imperative that the therapeutic radionuclide remain firmly associated with the radioactive drug in vivo for extended periods of from a few hours up to several days. The length of time required will depend upon the pharmacokinetic and physical half-life of the radionuclide. No single radionuclide will be appropriate in formulating therapeutic agents since different half-lives and the energy of emitted particles will be required for different applications [4–7], making it essential that radiopharmaceuticals with different radionuclides be made available.

It is expected that therapeutic agents will be primarily labeled with beta-particle emitting radionuclides for the near future. Several different chelating structures have been employed to maintain the association of these beta emitters with the drug [8–12]. Many of the chelating structures are not sufficiently stable and most, if not all, do not provide appropriate routes or rates of clearance of radioactivity from non-target tissues [13,14]. This results in delivery of high radiation doses to normal tissues and reduces the therapeutic ratio which in turn lowers the amount of radiation dose that can be safely delivered to target tissues, such as tumors or micrometastases. Development of new radionuclide chelates that link the radioactive metal to the radiopharmaceutical is presently necessary. These complexes must be highly stable in vivo while attached to the biomolecules and have improved clearance characteristics from normal tissues after catabolism of the antibody.

Diethyltriaminepentaacetic acid (DTPA) forms a rather stable chelate with a variety of metals and is exemplary of prior art chelating moieties. However, coupling of this ligand to monoclonal antibodies by one of its five carboxyl groups resulted in unacceptable in vivo stability with a variety of radionuclides [15]. Linking of DTPA by a side group attached to one of the carbon atoms on an ethylene bridging group provides improved in vitro and in vivo stability [16]. However, the stability characteristics are not ideal and clearance activity from certain organs such as kidney and liver, are poor [17].

Chelating agents based on the diamidodithiol (DADT) and triamidomonothiol (TAMT) backbones are another example of chelating agents that are used for forming small and stable hydrophilic complexes with $^{186}$Re, $^{188}$Re and $^{99m}$Tc [18,19]. Since the chelation chemistry of $^{99m}$Tc and Re are often identical [20], compounds labeled with $^{99m}$Tc, using the same bifunctional chelating agents used for $^{186}$Re/$^{188}$Re, should also make useful diagnostic imaging agents. There are presently labeled monoclonal fragment products for diagnostic and therapeutic applications being made [21]. These immunochelates provide improved clearance characteristics from the liver, however, kidney retention of activity when using Fab or F(ab)$_2$ fragments of monoclonal antibodies labeled with these radionuclide chelates is higher than desirable [22].

Another example is the macrocyclic tetraamine-based chelating agent that also has four methylene carboxylate side arms (teta or DOTA) that has been used to form a $^{67}$Cu complex that has high in vitro and in vivo stability when linked to monoclonal antibodies. This chelate was first described for monoclonal antibody bioconjugation by Meares and coworkers [23]. This is a large chelate that shows promise, however, clearance activity from non-target organs such as liver and kidney have not been shown to be more efficient than the DADT or TAMT type chelates.

Other non-antibody based radiodiagnostic or radiotherapeutic agents (e.g., chelates, small peptides, receptor agents) have also been considered for applications in humans [24–27]. New types of these agents would also be valuable where firm linking of the radionuclide to these compounds may also prove beneficial.

Diagnostic Agents $^{99m}$Tc has nearly ideal physical properties to formulate diagnostic radiopharmaceuticals for use as imaging agents in Nuclear Medicine. Because of these properties, it is the most widely used radionuclide for nuclear medicine studies in the world. Many $^{99m}$Tc chelates have been made for in vivo assessment of a wide variety of normal or diseased organ systems such as heart, brain, liver, kidney, thyroid, bone, etc. [28]. A variety of different chelation systems have been used in the design of these diagnostic radiopharmaceuticals [29]. The $^{99m}$Tc-chelates used in nuclear medicine involve complexation of the reduced Tc core with numerous donor atoms that are attached to a single chelating ligand or to several ligands.

The diagnostic $^{99m}$Tc agents used in nuclear medicine have different properties that provide them with specificity for functional localization in body organs or tissues. For example, neutral-lipophilic $^{99m}$Tc-chelates are presently being used as regional perfusion imaging agents for brain and heart muscle [30,31]. Cationic lipophilic $^{99m}$Tc complexes are used to assess regional myocardial perfusion [32,33]. $^{99m}$Tc complexes are also used as imaging agents for the study of hepatobiliary function [34], kidney function [35], tumor biolocalization [36] and for a variety of other purposes. Other $^{99m}$Tc chelates have been used as a vehicle for labeling proteins and monoclonal antibodies through conjugation techniques.

Contrast Agents

Metals with high nuclear spins have been shown to be useful for formulation of paramagnetic molecules that can be used as contrast agents in magnetic resonance imaging [37,38]. They are effective in providing important diagnostic information that assists in treatment of diseases in patients. It is important that these paramagnetic metal-complexes have some specific localization to provide contrast in the MRI signal in diseased or abnormal tissues relative to normal tissues. Only a few MRI contrast agents have been produced since this is a new and emerging field [39]. Clearly, additional MRI contrast agents are needed to provide improved agents and expand the diagnostic capabilities of MRI using these paramagnetic pharmaceuticals.

Mn and Fe are both transition metals with a high nuclear spin. Because of their paramagnetism, complexes with these metals that have high in vivo stability can make effective MRI contrast agents. New chelates can be used as a basis to formulate new agents with better specific localization properties that will permit imaging of sites of abnormalities in patients that cannot currently be imaged or will result in improvements in contrast enhancement compared to the agents available.

Phosphinimine Ligand Utilization

Phosphinimines have been polymerized for use in aerospace, implants, encapsulants, etc. Phosphinimines have not been successfully utilized at the single molecular level and have not before been applied for radiotherapy or for medical imaging. Despite the variety of ligand systems previously used, there are no reports of radionuclide complexes made using $R_3P=N$ phosphinimine ligands.

SUMMARY OF THE INVENTION

A class of diagnostic and therapeutic compounds derived from phosphinimines that include ligands containing only a single phosphinimine functionality or contain both a phosphinimine group and a phosphine or arsine moiety or an aminato moiety or a second phosphine amine moiety.

The present invention further provides a method of using phosphinimine based derivatives including the steps of complexing the ligand with radionuclides selected from the early and late transition metal group including $^{99m}$Tc, $^{186}$Re/$^{188}$Re, $^{109}$Pd, administering mCi amounts allows for localization of the complex at a predetermined site for radioimaging or for radiotherapeutic application.

The present invention further provides a method of using phosphinimine ligands, including the steps of complexing the ligand with paramagnetic transition metal ions such as $Mn^{+2}$, $Cr^{+3}$, $Fe^{+3}$, $Gd^{+3}$, $Dy^{+3}$ and $Ho^{+3}$, administering an amount of the complex to allow for localization of the complex at a predetermined site as a paramagnetic contrast agent for magnetic resonance imaging (MRI).

DETAILED DESCRIPTION OF THE INVENTION

The present invention provides a class of diagnostic and therapeutic compounds generally comprising phosphinimine ligands complexed with a transition metal. The complexes have high in vitro and in vivo stability over a wide pH range. More specifically, phosphinimine complexes of transition metals are compounds where the ligand structures have the general formula —N=PR$_3$, designated below as formula '1'. This group is isoelectronic with the corresponding phosphorane oxide, designated below as formula '2'. Both types of ligands form stable complexes with Lewis acidic transition metal halides and oxides.

$$N = PR_3 \quad (1)$$

$$O = PR_3 \quad (2)$$

In addition to the mondentate phosphinimine ligand described above, heterdifunctional phosphinimine ligands have also been formulated where a second functionality has been added to provide additional flexibility or stability in designing new complexes with transition metals. Examples of these heterodifunctional phosphinimine ligands are as follows:

A. Phosphinimine/Phosphine or Arsine Ligands

A subclass of this type of bidentate phosphinimine ligand is the ligand structure described below replacing the phosphinimine group with phosphine oxide group since both these groups are isoelectronic and should exhibit similar chelation properties.

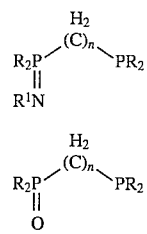

Both of these heterodifunctional phosphinimine type ligands will have strong affinity for early and late transition metals. The nonoxidized phosphine groups can be an arsine moiety. These ligands form complexes with transition metals represented by the following formula.

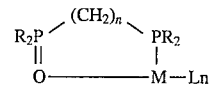

B. Phosphinimine—Amidates Ligands

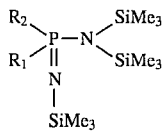

This ligand has strong affinity for early and late transition metals. These ligands form complexes with transition metals represented by the following formula:

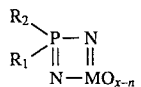

C. Bisphosphinimine Ligands

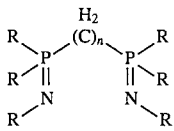

This bis-phosphinimine ligand has strong affinity for early and late transition metals and form complexes with these metals represented by the following formula:

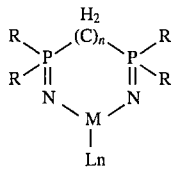

PHOSPHINIMINES

The phosphinimine ligand framework is electronically very versatile as a 1, 2 or 4 electron donor to transition metals resulting in M—N multiple covalent bonds wherein M is the transition metal. Synthetic approaches to phosphinimine complexes are varied and have resulted in the synthesis of stable and well-characterized complexes of some first, second and third row "early" transition metals [40,41].

Although a recent report describes the synthesis of a Re(VII) complex in which phosphinimine is only a part of a larger molecule [42], there are no reports on the potential utility of phosphinimine types of complexes for use as diagnostic or therapeutic agents. For example, there are no reports particularly concerning the formulation or application of radiopharmaceuticals with $^{186}Re/^{188}Re$, $^{109}Pd$, $^{105}Rh$ and $^{99m}Tc$ radionuclides. Furthermore, neither the synthesis nor potential utility of phosphinimine complexes with iron or manganese for use as magnetic resonance imaging (MRI) contrast agents have been reported. There are also no examples of the these types of complexes with any other transition metal radionuclides despite the synthetic, structural and chemical diversity offered by such ligands. Thus, the present invention provides synthesized phosphinimine complexes of transition metals (e.g., $^{99m}Tc$ or $^{186}Re/^{188}Re$, $^{109}Pd$, $^{105}Rh$, Mn, Fe) with an ultimate objective of providing diagnostic and therapeutic agents.

The phosphinimines can be obtained in mono, di polydentate forms. They combine the reactivities of hard nitrogen base soft π-acid phospines (e.g. in (RN) PR$_2$CH$_2$PR$_2$). Therefore, such ligands present the potential of being used as versatile chelating systems to a variety of metallic radioisotopes for diagnostic and therapeutic applications in nuclear medicine. For example, the metallic radioisotopes of diagnostic importance which can be complexed with the phosphinimine ligands include: $^{99m}Tc$, $^{111}In$, $^{67}Ga$, $^{68}Ga$, $^{62}Cu$, $^{97}Ru$, $^{103m}Rh$. Phosphinimine based ligands are equally useful for complexation with the radioisotopes of therapeutic importance that include α emitters e.g.; $^{212}Bi$, $^{211}At$; Auger-electron emitters e.g. $^{103m}Rh$, $^{165}Er$, $^{119}Sb$, $^{197}Hg$, $^{97}Ru$, $^{67}Ga$, $^{193m}Pt$; β emitters e.g.; $^{165}Dy$, $^{109}Pd$, $^{186/188}Re$, $^{166}Ho$, $^{153}Sm$, $^{90}Y$, $^{177}Lu$, $^{169}Er$, $^{105}Rh$, $^{149}Pm$, $^{67}Cu$, $^{199}Au$, $^{117m}Sn$.

As discussed in greater detail below, the ligand is strongly bound to the transition metal or the ligand can be used to chelate a metal. Preferably, there is a 1:1 metal-to-ligand ratio for the radiolabeled compounds. The phosphinimine complexes containing the 1:1 metal-to-ligand ratio result in the molecule R$_3$P=N—M-core which is small, may be linear, and well defined. Such ligands permit formation of the complex in a simple, 1 or 2 step, high yield reaction which utilizes readily available forms of the radionuclide (e.g., $^{99m}TcO_4^-$, $^{186}ReO_4^-$, Fe or Mn chlorides, as well as others).

The reactivity of $^{99m}Tc$, $^{186}Re/^{188}Re$ and other radionuclides with the variety of ligands which include phosphines, alkylisocynides, amineoximes, aminothiols, dithiocarbamate, and many macrocyclic amines have been the subject of radiopharmaceutical chemistry investigations which has been directed at developing diagnostic or therapeutic radiopharmaceuticals for use in nuclear medicine [43]. However, problems such as lack of stability and chemical flexibility of the ligand structures is associated with most of the above ligands and have caused problems in meeting stringent performance specifications of the radiopharmaceuticals to be used in the diagnostic and therapeutic applications [8,44–46]. The present invention presents an entirely new facet in fundamental coordination chemistry with a range of radionuclide or paramagnetic transition metals. The phosphinimine ligands offer a high degree of chemical flexibility that will be useful in designing new diagnostic or therapeutic agents. Compounds made in accordance with the present invention can be defined by the following formula:

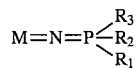

where R$_1$, R$_2$, and R$_3$, are hydrogen, halogen, amino, amide, alkyl, alkoxyl, alkenyl, alkynyl, aryl groups (incl. benzyl and phenyl derivatives), a transition metal radionuclide (incl. $^{99m}Tc$, $^{186}Re/^{188}Re$, $^{105}Rh$, $^{109}Pd$), Fe, or Mn; and Ln is oxygen and/or a halogen. The potential uses of the above defined compounds in medicine are substantial in both diagnostic and therapeutic nuclear medicine and as contrast agents for MRI imaging. More specifically, some of the nucleophilic $^{99m}Tc$-phosphinimine chelates are smaller than any previously identified. For example, (CH$_3$)$_3$—P=N—TcO$_3$ has molecular weight of only 237 daltons. Since the R groups can be varied, the polarity, charge, size, and lipophilicity can be systematically varied for maximum flexibility in Tc chelate design. Thus, the chelate system has the potential to be used for the design of regional cerebral perfusion imaging agents which require using small, neutral-lipophilic chelates [30]. The chelates system can also be used for myocardial perfusion imaging agents, using small to larger neutral-lipophilic chelates [47]. Hepatobiliary imaging agents can be made in accordance with the present invention using +1 or −1 charge lipophilic chelates [34]. The chelate system has a potential for use as renal (functional) imaging agents using small, charged and hydrophilic chelates [35]. A further example of the use of the present invention would be in cell labeling wherein these neutral lipophilic chelates would be able to readily defuse through cell membranes [28].

In addition to the above listed uses, the ligand system provides a unique opportunity for labeling compounds that have receptor binding activity with $^{99m}$Tc [25,26]. For example, the P=N—Tc linkages can produce products that are neutral and lipophilic. This is the most compact linkage known that has high stability, particularly since this system requires only a single, strong backbone to link Tc to the molecule, such as by the phosphine center. Furthermore, the N-unit of the heterodifunctional phosphinimine ligands can be derivatized with groups for attaching to receptor molecules to form radiolabeled receptor agents. For these reasons, the phosphinimine class of ligands held greater potential than the multidentate chelate systems based on C-backbones, such as diaminedithiol ligands now under investigation for preparing receptor imaging agents [25, 52–54].

The phosphinimine ligands can be mono dentate bidentate or multidentate; the structural diversity shown below clearly makes them highly versatile.

Monodentate $R_3P=N=SiMe_3$
R=CH$_3$ , C$_2$H$_5$—alkyl groups; OCH$_3$ , OC$_2$H$_5$ , OCH$_2$CF$_3$
Ph, OPh; NMe$_2$, NEt$_2$, NHMe, NHEt—

Bidentate

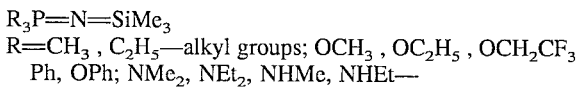

E=NH, O, S, (CH$_2$)n; n=1,2,3
R=Same combinations as listed for the monodentate above.

Multidentate

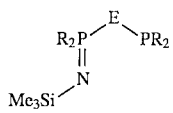

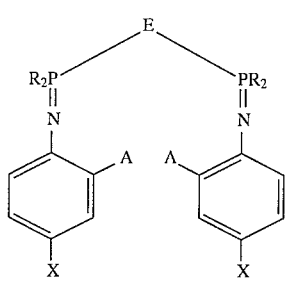

-continued

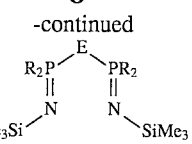

A=OH, SH COOH; X=OH, COOH
E=NH, O, S, (CH$_2$)$_n$; n=1,2,3
R=Same combinations as listed above for the mono and bidentates.

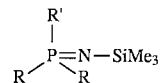

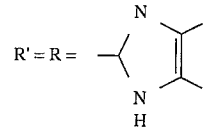

or R=combinations of substituents as listed above for the monodentate phodphinimines.

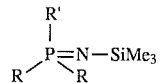

R'=R=—CH$_2$CH$_2$CN or CH$_2$CH$_2$CH$_2$NH$_2$ or R=combinations of the substituents as listed above for the monodentate phosphinimines.

Additionally, since the attachment of $^{99m}$Tc via the phosphinimine moiety is possible using $^{99m}$TcO$_4^-$ or by exchange labeling with a suitable donor molecule, these phosphinimine derivatives can be labeled by this technology in both aqueous and nonaqueous solutions as described below, providing a unique vehicle for preparing the $^{99m}$Tc or $^{186}$Re/$^{188}$Re labeled receptor agents.

As therapeutic agents, stable $^{186}$Re/$^{188}$Re complexes can readily be formed with the phosphinimine ligands in accordance with the present invention in high yields thereby providing for potential utility as in radionuclides therapy. For example, $^{186}$Re/$^{188}$Re can be complexed to the P—N derivatives for conjugating antibodies, antibody fragments, peptides, small receptor agents, or other biomolecules.

The ligands can also be complexed with Fe or Mn to use as potential paramagnetic MRI contrast agents. Since the phosphinimine ligands form stable bonds with most early transition metals, a variety of early transition metals with high nuclear spins can form complexes with potential application in MRI. The high stability of the P=N—M bonding systems and small size make them well suited for designing new contrast agents containing high spin Mn$^{+2}$, CR$^{+3}$. Fe$^{+3}$, Gd$^{+3}$, Dy$^{+3}$ and Ho$^{+3}$ based on the chelate systems.

Phosphinimine ligands are chemically flexible because chemical tuning at both the phosphorous and nitrogen center can be performed for effective complexations with a variety of paramagnetic metal ions the include Mn$^{+2}$, CR$^{+3}$. Fe$^{+3}$, Gd$^{+3}$, Dy$^{+3}$ and Ho$^{+3}$.

Monodentate Phosphinimine Ligands

In order to synthesize compounds in accordance with the present invention for use in the inventive method set forth herein, the monodentate phosphinimine ligand complexes can be made in accordance with the following reaction:

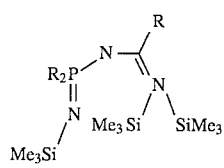

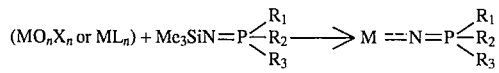

wherein M is Tc, Re, Pd, Rh, Fe, or Mn; X is a halide. $ML_n$ is a donor complex (e.g., glucoheptonate, citrate, pyridines, tertiary phosphines); $MO_nX_n$ being an oxyhalide or an oxide; and $R_1$, $R_2$ and $R_3$ are hydrogen, halogen, amino, amide, alkyl, alkoxyl, alkenyl, alkynyl alkyl carboxylic acid, aryl carboxylic acid, and derivatized benzyl or phenyl groups and all are the same or different, said reaction being in a nonaqueous environment or mixed aqueous-nonaqueous medium, or aqueous medium. Reactions of oxyhalides of radionuclides with the monodentate phosphinimine ligands result because the trimethylsilyl substituted aminophosphoranes have very high reactivity with transition metal halides because of their tendency to eliminate the leaving group $Me_3SiX$. The reactions take place according to the following stoichiometry:

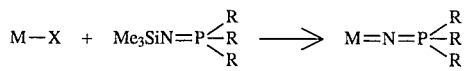

Bis-Phosphinimine Ligands

Skeletal flexibility and stability can be created through chelating diphosphinimines in accordance with the present invention with radionuclides as follows:

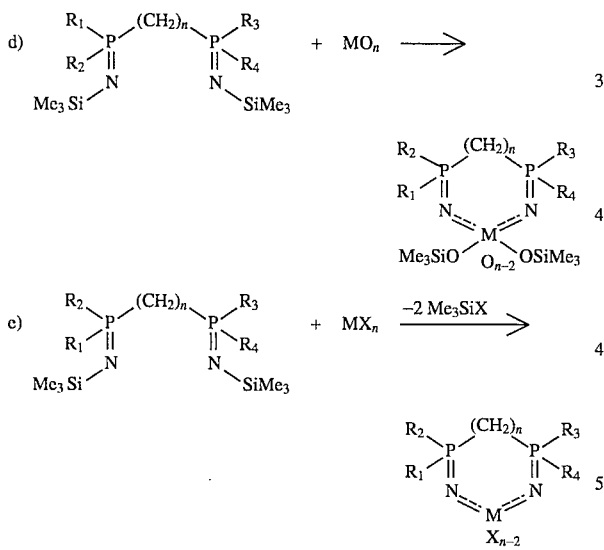

wherein X is chlorine or fluorine. In addition, metal chelates with these types of diphosphinimine ligands can be made by exchange labeling (e.g., MLn). $R_1$, $R_2$, $R_3$, $R_4$, $R_5$, $R_6$ are hydrogen, alkyl, alkoxyl, alkenyl, alkynyl, alkylcarboxglic acid, arylcarboxyliacid, and derivatized benzyl or phenyl groups and all are the same or different.

Phosphine-imine-amidates

Phosphinimines can be functionalized at the P-atom to produce an additional amido moiety for modifying chelation characteristics of the parent phosphinimine ligand. The scheme below illustrates the synthesis of these ligands.

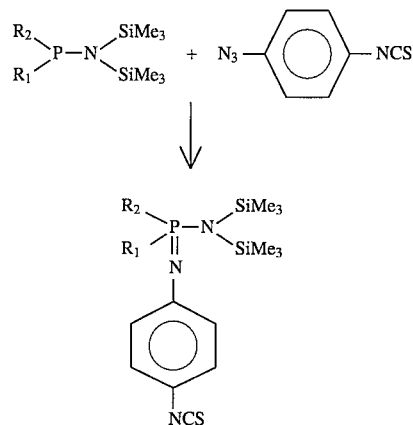

Metal ions can be complexed by these ligands by the following reaction:

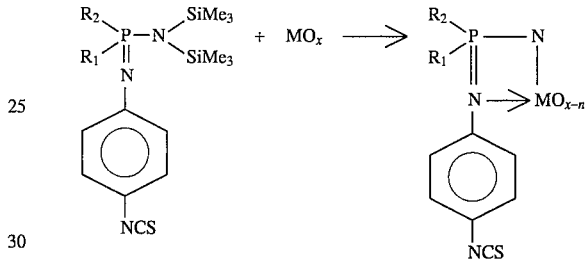

The addition of the amido group provides a vehicle for providing extra stability through conjugated metallocycle formation with different radionuclides as shown below using Tc as an example:

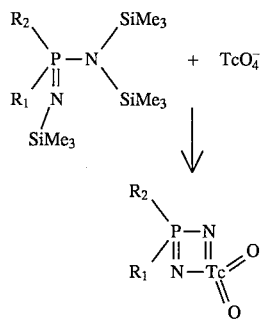

Either the amido or phosphinimine N-centers can be used to provide active sites for binding with other molecules (e.g., receptor agents, peptides, proteins, etc.). $R_1$, $R_2$ are hydrogen, alkyl, alkenyl, alkynyl, alkylcarboxylic acid, arylcarboxylic acid, phenyl or benzyl derivatives and all are the same or different. M is Tc, Re, Pd, Rh, Fe, Mn or other early or late transition metals.

Phosphinimine-Phosphine Hetero-difunctional Ligands

Incorporation of a phosphine (or arsine) group in molecules containing a phosphinimine moiety provides for further flexibility of the complexing properties of the basic phosphinimine ligands with transition metals. Specifically, with the presence of both the P=N and phosphine or arsine functionalities, transition metals with a wider variety of oxidation states can be complexed as compared to ligands containing only the phosphinimine donor group. In addition, the presence of the second donor atom on the molecule will provide substantial improvement in the complex stability. These ligands also provide greater opportunities for derivatization as different groups can be attached at both P-atoms, the P and As, the N-atom or the alkane group bridging the phosphinimine P-atom to the phosphine or arsine (P or As atoms), respectively. examples of the structures of ligands (PCPN and AsCPN) are shown below.

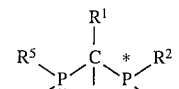

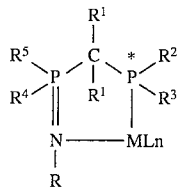

$R_1$, $R_2$, $R_3$, $R_4$, $R_5$, $R_6$, $R_7$ are hydrogen, alkyl, alkenyl, alkynyl, alkylcarboxylic acid, arylcarboxylic acid, phenyl or benzyl derivatives and all are the same or different. $R_7$ can be absent. M is Tc, Re, Pd, Rh, Fe, Mn or other early or late transition metals. P* can also be As.

For example the reaction of $PdCl_4^{31}$ with the PCPN ligand shown below has been prepared and chemically and radiochemically characterized.

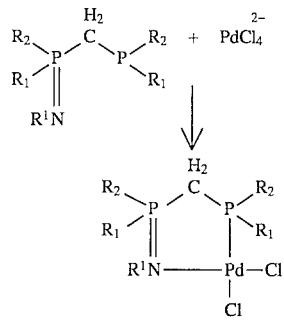

where R=Phenyl and $R^1=CH_3$.

Parallel chemistry replacing the N atom with an O-atom in the PCPN or AsCPN ligands has been performed to produce the respective PCPO and AsCPO ligands.

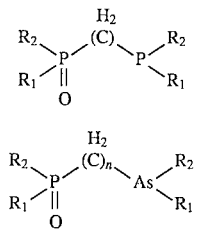

where $R^1$–$R^6$ are the same or different and are the same groups as designated for the PCPN ligands.

An example of this type of complex with Re has been prepared with a PCPO ligand as shown below:

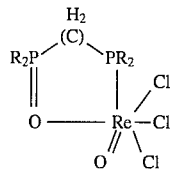

The transition metal complexes formed with these PCPN and PCPO ligands with these transition metals exhibit exceptional stability. For example, we have shown that $^{99m}$Tc as described for these PCPN and PCPO ligands can be used to produce agents for diagnostic radionuclide imaging (e.g. $^{99m}$Tc) or for radiotherapeutic purposes (e.g. $^{186}$Re/$^{188}$Re, $^{109}$Pd etc. ). In addition, their complexes with Mn or Fe could be used to prepare paramagnetic MRI contrast agents that have high stability. A systematic alteration of the substituents on the phosphorus in all these ligands is possible. This provides a useful mechanism to control the biodistribution properties of complexes with $^{99m}$Tc, $^{188}$Re, $^{109}$Pd, $^{105}$Rh and other transition metals. The P-Atom bound to Re can be replaced by an As atom to give the respective AsCPO ligand.

For example, the $^{99m}$Tc-PCPN complex exhibits preferential liver uptake in rats with phenyl groups as substituents on both phosphorus atoms. However, increased kidney clearance and decreased liver uptake of the complex was measured on changing the substituents to the methyl groups.

A wide variety of substituent variations can be performed to develop complexes with suitable biodistribution properties. PCPN (or AsCPM) ligands can be used for preparing radiolabeled conjugates of proteins, peptides or other molecules (e.g., receptor agents). These ligands can be linked to proteins or other molecules by functionalizing any of the R groups. However, a convenient method of attaching the PCPN (or AsCPN) ligand complexes, to other substances, is via the R group attached to the phosphinimine-N-atom. A controlled oxidation of one of the phosphines on an alkyldiphosphine can be accomplished using the Staudinger reaction [48]. This reaction involves the reaction one of the phosphine atoms with an azide group to produce the respective PCNP derivative. An example of this is shown as follows where p-azido-benzyliso thiocyanate reacts with an alkyl-diphosphine to readily produce the benzyl-isothiocyanate PCPN derivative.

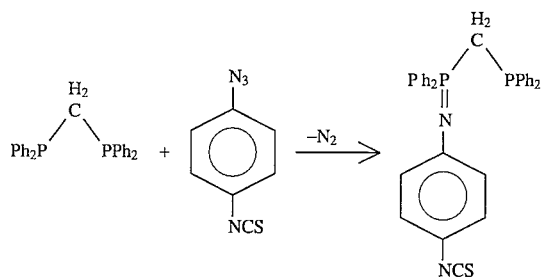

The corresponding AsCPN benzyl isothiocyanate derivative can be made by the same route as follows:

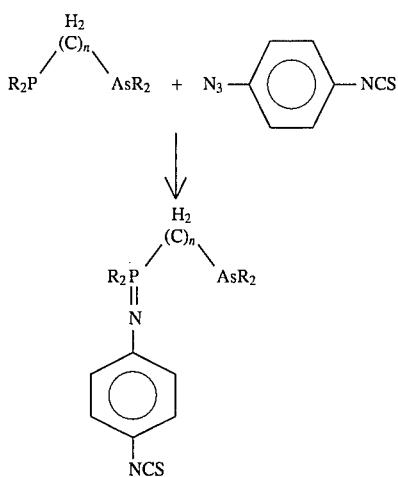

This derivative, was shown to react with $ReOCl_4^-$ to form the Re chelate in high yield as shown as follows:

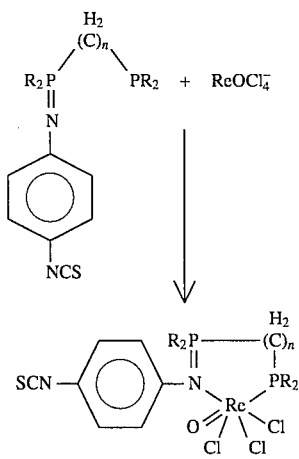

$^{188}ReOCl_4^-$ and $^{99m}TcOCl_4^-$ react in similar ways

This chelate was then shown to conjugate a large protein (i.e., IgG) efficiently (i.e., 70–85% yield) via the isothiocyanate coupling reaction [8,44–46] as shown below. PCNP or AsCPN ligands can also be similarly derivatized with other R-groups containing active proteins or peptides by other reactions (e.g., aldehydes, imidates, succinemides, alkyl bromides, etc. [8,44–46]).

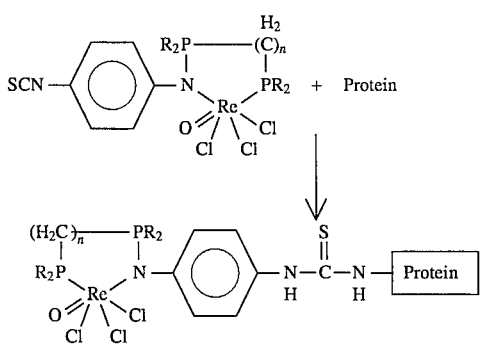

Using this approach, the phosphine and the phosphinimine functionalities can be used to chelate $^{99m}Tc$, $^{188}Re/^{186}Re$ and the conjugating group or other conjugating groups (e.g. succinimide, benzylisothiocyanate) or other metals can be made to link the chelate peptides or ligand proteins or monoclonal antibodies to other proteins or peptides. These new classes of bioconjugates based on phosphinimine ligands are unique because (a) they can be prepared in high purity and are stable so they can be stored; (b) they can be linked to the proteins prior to their conjugation with the radionuclides or after performed radionuclide complexes have been produced.

"Metal-Essential" Chelates

Metal-essential chelates are those in which the radioactive metal or paramagnetic metal forms a complex with a ligand that results in a compound with biolocalization characteristics that make it a useful diagnostic or therapeutic radiopharmaceutical or MRI paramagnetic contrast agent [39]. Neither the metal alone, nor the chelating agent, itself, will dictate biolocalization characteristics that are the same as the complex. Most radiopharmaceuticals or MRI contrast agents that are FDA approved are of this type.

The phosphinimine ligands described in this invention provide an entirely new chemical basis for formulation of a variety of metal-essential radiopharmaceuticals or paramagnetic contrast agents. With appropriate derivatization of the phosphinimine class of ligands, modification of the biolocalization properties of the respective metal-complexes should produce agents that have similar or superior properties for medical applications than agents currently in use. For example, derivatives of $^{99m}Tc$-phosphinimine chelates should make useful diagnostic agents to evaluate brain perfusion, myocardial perfusion, hepatobiliary function, kidney function, bone lesions, abscesses via WBC labeling, etc. As a specific example, appending a diphosphonate group to one of the phosphinimine ligands shown below should produce a chelator that will selectively complex $^{99m}Tc$ but selectively localize in normal and abnormal skeletal tissues.

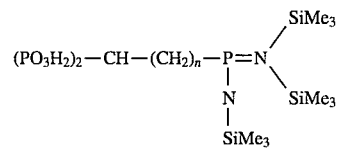

The possibility of preparing brain or myocardial perfusion imaging agents is made possible by the fact that most of the phosphinimine ligands can produce small neutral-lipophilic $^{99m}Tc$-chelates, a property important for appropriate in vivo localization in brain and/or the myocardium [30,47]. The neutral-lipophilic chelates may also prove useful for cell labeling [28]. $^{99m}Tc$-chelates with other organ specificities that are polar and/or charged can be produced by varying ligand substituents (e.g., adding carboxylate side chains) that will increase the rate of clearance through the kidney [28,29].

Similarly, beta emitting radionuclides (e.g. $^{186}Re/^{188}Re$, $^{105}Rh$, $^{109}Pd$, etc.) complexed with phosphinimine ligand derivatives should also form chelates with desirable biolocalization properties that will be useful for therapeutic applications. The phosphinimine ligand derivatives developed for $^{99m}Tc$, should have similar biolocalization properties with $^{186}Re/^{188}Re$ because of the chemical similarities between Tc and Re [32]. For example, a diphosphonate derivative of a phosphinimine chelate should produce a useful and chemically well-defined therapeutic agent for treatment of skeletal metastases [49]. Fe and Mn complexes with phosphinimine ligand derivatives that have high in vivo stability should form the basis for new agents with varying lipophilicity and charges for applications in MRI contrast enhancement imaging [37–39].

Receptor Agents

Two general classes of receptor agents have been utilized in nuclear medicine. One type is based on using peptides that bind specifically to receptors [26] and the other is based on non-peptide molecules that bind to receptors [25]. Both of these types of agents have been labeled with radionuclides for diagnostic imaging. Both of these types of agents depend upon the receptor agent to provide for specific in vivo localization and carrying the receptor or therapeutic radionuclide to the preferred site.

Peptide Receptor Agents

An example of a peptide receptor agent is the "$^{123}$I-tyr-octreotide" that has receptor binding activity that is similar to somatostaton [26]. This agent as well as this peptide labeled with $^{111}$In via a bifunctional chelating agent, has proven useful for localization of several different types of cancers (e.g., small cell lung Ca) that express the somatostaton receptor on their cell surface [26]. Clearly, the ability to readily label this or similar peptide-receptor agents with $^{99m}$Tc would provide an important advance in the field of receptor imaging. Because of the versatility of the phosphinimine ligands for derivatization, for readily forming $^{99m}$Tc complexes and their high degree of stability, bifunctional chelating agents (BFCAs) or bifunctional chelates (BFCs) based on the phosphinimine ligands described in this invention should provide an appropriate vehicle for labeling peptides with $^{99m}$Tc. An example of this approach is described as follows:

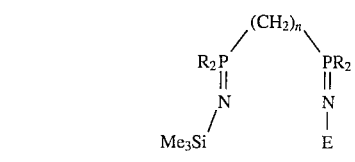

I and

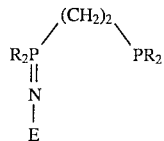

II (E is an active site for protein)

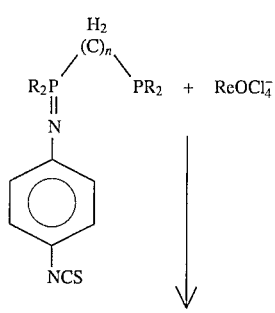

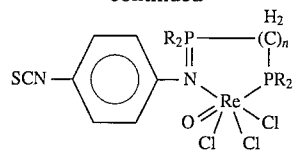

$^{188}$ReOCl$_4^-$ and $^{99m}$TcOCl$_4^-$ react in similar ways

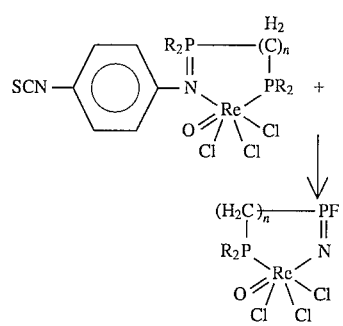

In this scheme, the benzylisothiocyanate derivative of the tetramethyl PCPN ligand is synthesized by using the Staudinger reaction [48] that results in a high yield reaction of one of the phosphine groups on the tetramethyldiphosphine ligand with p-isothicyanato-phenylazide. $^{99m}$TcO$_4^-$ was then reacted with the resulting product to produce the $^{99m}$Tc-PCPN-isothiocyanate BFC. This BFC can be linked to the peptide via the $\epsilon$-amino group on lysine. This results in a $^{99m}$Tc-labeled peptide that is stable for $\geq 24$ hr in saline and serum.

Alternatively, the BFCA or the phenylisothiocyanate derivative of the uncomplexed tetramethyl PCPN ligand can be conjugated by the same route. After separating excess unconjugated ligand, the $^{99m}$Tc could be specifically complexed to the appended PCPN group via exchange labeling [50]. Several different donor chelates could be used for the exchange labeling method (including $^{99m}$Tc-citrate, -glucoheptenate, -tetrapyridinel, a ditriphenylphosphine trichloro Tc(V)-oxo complex). In addition, other methods to conjugate the ligand to peptides or proteins can also be used (including an activated ester, bromo-alkylation, succinimide, imidate, etc. [44–46]). A variety of phosphinimine ligands, based on those previously described, can be used for this application, as long as the resulting phosphinimine component of the BFCA has appropriately high stabilities with $^{99m}$Tc. Similar approaches can be used for labeling receptor peptides with beta-emitting transition metal radionuclides via phosphinimine-based BFCAs or BFCs. These types of labeled peptides could be used for unsealed source radiotherapeutic applications as long as the biolocalization in target tissues (including cancers) has sufficient in vivo specificity. Any BFCAs or BFCs found to be useful in preparing $^{99m}$Tc-labeled receptor peptides should be equally useful for preparing $^{186}$Re/$^{188}$Re labeled for therapeutic applications agents since the chemistry of Tc and Re are often identical.

Non-peptide Receptor Agents

The other type of receptor agents are usually smaller than peptides causing their binding to be affected by appending new radionuclides or BFCAs. Some of these agents cannot tolerate relatively minor structural modifications and would not be considered for use with $^{99m}$Tc or other transition metal radionuclides. There are, however, some receptor agents that will tolerate the presence of a BFCA or BFC at a site removed from the part of the molecule that specifically interacts with and binds with receptors [25]. Even though these receptor agents will tolerate some bulk at remote sites, the smaller labeled moieties at these sites should interfere less with specific binding. Furthermore, since most of the receptor agents have a high degree of lipophilicity and must bind to receptors in cell membranes, the resulting labeled receptor must retain a reasonable amount of lipid solubility. Thus, the $^{99m}$Tc-chelate used for labeling these types of receptors should most likely be neutral with at least some lipophilic character. Several of the $^{99m}$Tc-labeled phosphinimine derivatives qualify on both the considerations. First, some of these fundamental phosphinimine chelating groups are smaller than most, if not all, $^{99m}$Tc-chelating moieties used in radiopharmaceuticals. In addition, they can be made neutral and lipophilic. The specific differences in lipophilicity of the appended $^{99m}$Tc should have important effects on target/non-target binding of the receptor agents [25].

In addition to these considerations, the ease of formation of single, well defined $^{99m}$Tc-receptor agents using labeling techniques that are simple, versatile and high yield reactions are important considerations in preparing FDA approved radiopharmaceuticals. Again, many of the phosphinimine ligands meet these criteria making them ideally suited for this purpose. For example, the formation of the following neutral-lipophilic product that has high stability was formed in high yield by the following reaction.

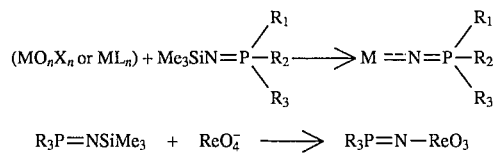

$$R_3P=NSiMe_3 + ReO_4^- \longrightarrow R_3P=N-ReO_3$$

This reaction took place in aqueous solution. Another advantage the phosphinimine ligands offer is that complexation can be accomplished concurrently in non-polar solvents. This may be particularly important for being able to readily label receptor agents that have minimal solubility in aqueous solutions. Furthermore, obtaining a high yield starting with $^{99m}$TcO$_4^-$ as the reactant using a ligand dissolved in a non-polar solvent would be particularly useful for clinical nuclear medicine applications since $^{99m}$Tc is readily available from FDA approved $^{99}$Mo/$^{99m}$Tc-generators as the pertechnetate anion. For example, the following neutral-lipophilic $^{99m}$Tc-phosphinimine chelate was produced in >90% yield by simply mixing $^{99m}$TcO$_4^-$ in saline with the ligand dissolved in acetonitrile or dichloromethane demonstrating the feasibility of this approach with these types of ligands.

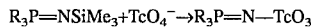

$$R_3P=NSiMe_3+TcO_4^-\rightarrow R_3P=N-TcO_3$$

This approach could be extended to the application where a receptor agent conjugated to a phosphinimine ligand that is dissolved in a non-polar solvent could be readily labeled with $^{99m}$Tc. Clearly, other chemical forms of $^{99m}$Tc, in either polar or non-polar solvents, could also act as the reactant to form the $^{99m}$Tc-labeled receptor agent via its complexation with a conjugated phosphinimine ligand.

Despite advances in the bioconjugation of the many ligating systems now in use to attach $^{99m}$Tc or $^{188}$Re complexes to the biomolecules, many problems remain which have restricted the practical utility of the new sophisticated vectors that could be labeled with $^{99m}$Tc (or $^{188}$Re) in humans. Specifically, specific labeling of chelating agents conjugated to proteins or other molecules with $^{99m}$Tc (or$^{188}$Re) requires the use of a reduced form of Re or Tc (i.e., oxidation state ≦5). Since $^{99m}$Tc and $^{188}$Re are only readily available in aqueous solutions for medical purposes as Tc(VII)-pertechnetate or Re(VII)-perrhenate, these radiometals must be reduced with another reducing agent (e.g., Sn(II)) to a lower oxidation state to elicit binding to the conjugating chelating agents. Unfortunately, this causes severe problems, that have not been satisfactorily overcome, when trying to properly label biomolecules. In particular, reduced Tc or Re (e.g., Tc(V)) or Re(V) will hydrolyze in water, can be easily oxidized back to the +7 states and can non-specifically bind to undesirable sites on the biomolecules [8,51]. If it were possible to react either $^{99m}$TcO;or $^{188}$ReO- directly with a complexing agent conjugated to the biomolecule (e.g. protein), without the reductio step, it would represent a major technological breakthrough for labeling a variety of molecules with $^{99m}$Tc or $^{188}$Re.

Recent studies in applicants' laboratories have clearly demonstrated that by simple mixing of ReO$_4^-$ in aqueous media with R$_3$P=N—SiMe$_3$ (R=Ph) ligand dissolved in a non-polar solvent (e.g., toluene or CHCl$_3$) produced the stable ion pair, Ph$_3$P=HN$_2$+ReO$_4^-$, In near quantitative yields. The structure of this compound was confirmed by NMR, IR and X-ray crystallography (Scheme 1). Upon heating this ion pair, either in the solid state or in solution, dehydration occurred and resulted in the formation of the "neutral Re(VII) phosphinimine complex". This is the first example of a stable completx of phosphiniminato Re(VII) .

This reaction sequence was repeated using $^{99m}$TcO$_4^-$. Typically, 5–20 mg of Ph$_3$PNSiMe$_3$ dissolved in 1 ml of toluene was vortexed with 0.1 ml N-saline containing 1–10 mCi$^{99m}$TcO$_4^-$. After vortexing for 1 minute >95% of $^{99m}$Tc was found in the toluene layer. Interestingly, the $^{99m}$Tc complex (i.e., the ion pair) was mobile with both C-18 reversed phase TLC with an 80/20; Acetonitrile/H$_2$O mobile phase (R$_1$=0.9). After heating the organic layer at 60° C., the resulting $^{99m}$Tc complex (i.e., presumably Ph$_3$P—N—TcO$_3$) had an R$_1$ of 0.4 on C-18-TLC.

It must be emphasized that this phosphinimine class of ligands is the only known ligand system capable of strongly interacting the $^{99m}$TcO$_4^-$ or $^{188}$ReO$_4^-$ and provides an unique approach for creating an ideal method for labeling of biomolecules for medical applications.

Though the stability of the Ph$_3$PN—TcO$_3$ "neutral complex" is excellent in organic media (e.g., toluene) it will convert over time back to the ion-pair form in aqueous media. Modification of the basic phosphinimine ligand by adding one or more chelating groups in addition to the phosphinimine moiety should retain their unique capability to react directly with TcO$_4^-$ and ReO$_4^-$ and form stable Tc(VII) or Re(VII) complexes in aqueous media. Examples of these types of derivatized phosphinimine ligands are shown above.

Very recently tributylphosphinimine [(nBu)$_3$PNH] was synthesized, shown to be soluble in water and readily forms a complex by simply mixing it with $^{99m}$Tc (no reducing agent was added). The structure and properties of this new complex have not been determined, however this preliminary data does demonstrate that complex formation, with appropriate phosphinimine ligands, using only TcO$_4^-$ (and presumably ReO$_4^-$) can occur in an entirely aqueous medium. New water soluble phosphinimines should maximize the complexation yield and the stability of the respective Tc (VII) and Re (VII) complexes. If a stable phosphinimine complex with Re(VII) or Tc(VII) can be formed that has high in vivo and in vitro stability this would make it feasible to label biomolecules with the corresponding phosphinimine ligand by simple means using the conjugated $^{186/188}ReO_4^-$ or $^{99m}TcO_4^-$.

Tributylphosphinimine $(SiMe_3N=P[(CH_3)(CH_2)_3]$ was prepared as follows; tributylphosphinimine (15 g; 74 mmol) was added dropwise to azidotrimethylsilane (50 g; 434 mmol) placed in round bottom flask fitted with a reflux condenser under an envelope of nitrogen gas. The mixture was refluxed in an oil both maintained at 135°–140° C. for 6 hours and was allowed to cool to room temperature before the excess of the azidotrimthylsilane removed under vacuo. The resultant oil was distilled under vacuum (165° C.; 10 mm Hg) to obtain analytically pure tributylphosphinimine. P-31 NMR(CDCl$_3$; 85% H$_3$PO$_4$) 2.00 ppm.

These phosphinimine ligands may also be useful for preparing stable Tc(V) or Re(V) complexes. By analogy to the method described by Thomas and Davison (55), once the PN—MO$_3$ (M-Re(VII) or Tc(VII) is formed, the metal may be reduced by a reducing molecule to form a Tc(V) or Re(V) phosphinimine complex that may have better stability than the Tc(VII) or Re(VII) precursor. This could provide or an important route for labeling biomolecules with $^{99m}$Tc or $^{186/188}$Re. Simply mixing the biomolecule conjugated with the appropriate phosphinimine ligand to form the respective ReO$_3^+$ or TcO$_3^+$ could then be specifically reduced in situ to form the respective $^{99m}$Tc(V) and $^{186/188}$Re(V) chelates.

Radiolabeled Immunoconjugates

Antibodies or antibody fragments (including F$_{AB}$, (F$_{AB}$)$_2$, other fragments) can be labeled with the phosphinimine type ligands outlined herein. The methods for conjugating the antibodies with either BFCAs or BFC's (i.e., preformed radionuclide BFCs) by the methods described for labeling peptides. In addition, BFCs and BFCAs based on these phosphinimine ligands can also be linked to the carbohydrate portion of whole antibodies using periodate oxidation followed by Schiff base coupling. The reaction outlined in Scheme A was performed with IgG using the preformed $^{99m}$Tc-labeled BFC. The labeling efficiency using 10$^{-5}$M IgG and 10 mCi of the $^{99m}$Tc-BFC was 70±5% at pH 9.0 after incubating the BFC with the IgG for 30 minutes. $^{99m}$Tc-labeled IgG was shown to be stable in saline at pH 9 for ≧36 hr.

Alternatively, a non-labeled BFCA based on phosphinimines could be also coupled to the antibody either using the activated conjugation reactor route (e.g., benzylisothiocyanate) or with an azide (e.g., benzylazide) already coupled to the Ab using the Staudinger reaction [48]. In this later method, conjugation of a benzylazide moiety to the Ab can be performed followed by characterization of the Ab (e.g., binding affinity). A diphosphine ligand can then be added in excess to specifically form the resulting heterdifunctional phosphinimine conjugate of the Ab as exemplified below:

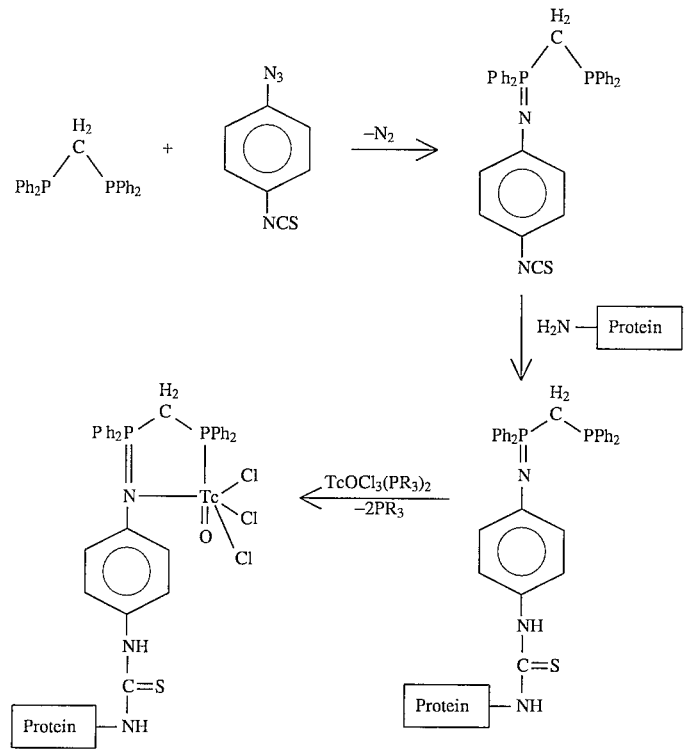

The resulting immunoconjugate can then be labeled by exchange labeling [8,12,44–46,50].

In addition to forming $^{99m}$Tc-labeled immunoconjugates by these methods via phosphinimine BFCs or BFCAs, other beta emitting transition radionuclides (including $^{186}$Re/ $^{188}$Re, $^{109}$Pd, $^{105}$Rh, etc.) or alpha-emittes or Auger-electron emitters may be used to form radioimmunotherapeutic agents. As previously described, the phosphinimines offer a great deal of flexibility in designing appropriate BFCAs and BFCs. Using these ligands as a basis for designing these conjugations, one can design small ligands with high lipophilicity or highly hydrophilic; this later type should clear rapidly from non-target tissues following catabolism of the antibodies or respective fragments. This will be important in being able to optimize the design of radioimmunotherapeutic agents.

Under FDA rules the phosphinimine complexes must be prepared immediately at the time of use. Therefore a kit made in accord with the present invention is used and contains a phosphinimine or phosphinimine derivative ligand and a transition metal selected from the group consisting of transition metal radionuclides (including alpha emitters, Auger-electron emitters, beta-emitters) and non-radioactive paramagnetic transition metals.

The complex is then formed according to the present invention and administering an amount of the complex to allow localization of the complex at a predetermined site in the body.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims, the invention may be practiced otherwise than as specifically described.

What is claimed is:

1. A method of using phosphinimine ligands includes the steps of: complexing the phosphinimine ligand with $^{99m}$Tc; administering to a body an amount of the complex to allow localization of the complex at a predetermined site in the body; and radioimaging the site by detecting the complex localized at the site.

2. A method of using phosphinimine ligands includes the steps of: complexing the phosphinimine ligand with a transition metal radionuclide selected from the group consisting of alpha-emitters, Auger-electron emitters and beta-emitters; administering to a body an amount of the complex to allow for localization of the complex at a predetermined site to provide a highly localized radiation dose to be delivered to the site for therapeutic or diagnostic treatment.

* * * * *